US010850049B2

(12) United States Patent
van Weteringen et al.

(10) Patent No.: US 10,850,049 B2
(45) Date of Patent: Dec. 1, 2020

(54) INSUFFLATOR

(71) Applicant: Erasmus University Medical Center Rotterdam, Rotterdam (NL)

(72) Inventors: Willem van Weteringen, Rotterdam (NL); Johnny Vlot, Rotterdam (NL); Tomas Gijsbertus Goos, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

(21) Appl. No.: 15/746,956

(22) PCT Filed: Jul. 23, 2015

(86) PCT No.: PCT/NL2015/050538
§ 371 (c)(1),
(2) Date: Jan. 23, 2018

(87) PCT Pub. No.: WO2017/014623
PCT Pub. Date: Jan. 26, 2017

(65) Prior Publication Data
US 2019/0160235 A1    May 30, 2019

(51) Int. Cl.
*A61M 13/00* (2006.01)
*A61M 16/00* (2006.01)

(52) U.S. Cl.
CPC ........ *A61M 13/003* (2013.01); *A61M 16/024* (2017.08); *A61M 16/0006* (2014.02); *A61M 2016/0021* (2013.01); *A61M 2016/0027* (2013.01); *A61M 2016/0036* (2013.01); *A61M 2205/3334* (2013.01); *A61M 2205/3344* (2013.01)

(58) Field of Classification Search
CPC ... A61M 13/003; A61M 13/00; A61M 13/006
See application file for complete search history.

(56) References Cited

U.S. PATENT DOCUMENTS

| 4,686,974 A | 8/1987 | Sato et al. |
| 4,971,034 A | 11/1990 | Doi et al. |
| 2004/0221854 A1 | 11/2004 | Hete et al. |
| 2005/0222491 A1 | 10/2005 | Noda et al. |

(Continued)

OTHER PUBLICATIONS

European Paetnt Office, International Search Report in corresponding International Application No. PCT/NL2015/050538 dated Apr. 14, 2016 (3 pages).

*Primary Examiner* — Emily L Schmidt
(74) *Attorney, Agent, or Firm* — Leydig, Voit & Mayer, Ltd.

(57) ABSTRACT

An apparatus is disclosed intended to expose a structure within a cavity of the human body for therapeutic and/or surgical treatment. The apparatus comprises an insufflator, comprising a gas output and an insufflator input mechanism adapted to input the gas from the gas output into the cavity of the human body, further comprising an insufflator controller for enlarging the cavity part by insufflation of gas from the gas output into the cavity; and a breathing rate detector; wherein the insufflator controller is arranged to real time adapt an insufflation frequency rate and flow in accordance with a detected or set breathing rate of the human body.

14 Claims, 10 Drawing Sheets

(56) References Cited

U.S. PATENT DOCUMENTS

2006/0047184 A1 3/2006 Banik et al.
2007/0244363 A1* 10/2007 Sano .................. A61B 1/00039
600/158

* cited by examiner

INSUFFLATOR

CROSS-REFERENCE TO RELATED APPLICATIONS

This patent application is a U.S. National Phase of PCT International Application No. PCT/NL2015/050538, filed Jul. 23, 2015, which is expressly incorporated by reference in its entirety, including any references contained therein.

FIELD

The present invention relates to an insufflation apparatus intended to expose structures within a cavity of the human body, by insufflating gas into that body cavity, to obtain a field of vision, through the endoscope, to perform a diagnostic and/or therapeutical endoscopic procedure to that structure in the body cavity. The apparatus further relates to a computer controlled method of operating an insufflator intended to expose structures within a cavity of the human body for a diagnostic and/or therapeutic endoscopic procedure.

BACKGROUND

The application of minimal access surgery, allowing surgery through a few small incisions by introduction of a camera and instruments, has become the standard for most surgical procedures. In the thorax and abdomen a surgical field is created by the insufflation of carbon dioxide gas to the desired pressure level. Due to the fact that the first explorations of body cavities were performed by manually insufflating air through a needle, the insufflation of gas into the abdomen is nowadays still called 'pneumoperitoneum', or 'pneumothorax' for the thoracic cavity. First pioneered by Raoul Palmer in 1943, he already used carbon dioxide for its non-combustive properties in the presence of electrical cauterization instruments. Endoscopy, in which a small diameter instrument allows looking within the body, was now possible. The introduction of proximal illumination endoscopy in 1952 was a breakthrough, delivering enough light to adequately perform procedures. However, the need for manual insufflation of carbon dioxide gas made the surgical working space quite difficult to maintain. To create a stable pneumoperitoneum, Kurt Semm invented an automatic insufflator in the 1960's. This insufflator maintained the intra-abdominal pressure at a set value, automatically limiting the flow when the pressure was reached. Also the insufflated volume of gas was registered. Since Kurt Semm built the first insufflator, the machine as it is used today remains remarkably similar in design.

Overcoming technical difficulties and the need for miniaturization of instruments, minimal access surgery is nowadays possible even in the smallest of children. The principles of insufflation remain yet the same; a volume of carbon dioxide gas is insufflated into the thoracic or abdominal cavity to create working space to allow surgery. Insufflation of pressurized gas however has several negative consequences. One of these factors is the uptake of the insufflated carbon dioxide gas into the blood due to the increased partial pressure of this gas around the tissues, adding to the normal production of carbon dioxide which we normally exhale to dispose of. By artificially increasing the carbon dioxide levels in the blood through insufflation, a larger amount of carbon dioxide has to be removed from the patient's system by ventilation during minimal access procedures. Another problem is the occupation of space by the volume of the insufflated gas. The insufflated gas presses against the diaphragm or lungs, hence competing with the required pressure to mechanically ventilate the patient. With less space for the lungs to move, higher pressures are needed to adequately ventilate the carbon dioxide, which can cause barotrauma to the lungs.

Current insufflators insufflate $CO_2$ gas up to a preset pressure with a maximum set flow rate. The $CO_2$ gas pressure is maintained by measuring at a relatively low frequency of 1 Hz or lower. The insufflated $CO_2$ volume is a relatively static volume, due to the fact that the current equipment does not have the ability to adjust the volume per ventilated breath, especially in the case of high frequency oscillatory ventilation (HFOV). As a consequence, high airway pressures have to be applied to distend (and thereby ventilate) the lung with each breath.

SUMMARY

In an aspect of the invention there is provided an apparatus and a computer controlled method having the features listed in the independent claims. In particular, the invention pertains to an apparatus intended to expose structures within a cavity of the human body for a diagnostic and/or therapeutic endoscopic procedure, comprising an insufflator. The insufflator comprises a gas output and an insufflator input mechanism adapted to input the gas from the gas output into the cavity of the human body, further comprising an insufflator controller for enlarging the cavity part by insufflation of gas from the gas output into the cavity. A breathing controller is provided, and the insufflator controller is arranged to real time adapt an insufflation frequency rate in accordance with the breathing controller. Alternatively the insufflator can generate an insufflation rate which can be output to the ventilator, if needed in combination with the applied pressures and/or flow rates.

In some embodiments, the invention pertains to vary the pressure and/or volume of insufflated $CO_2$ in a reciprocal manner with each ventilated breath, decreasing the pressure strain on the lungs and easing artificial ventilation. This can be applied to conventional mechanical ventilation (CMV), in which tidal volumes and frequency are close to what is physiological, but also in high-frequency ventilation (HFOV), in which very small tidal volumes are given at a high frequency. The reduced pressure variation in HFOV is beneficial to the lungs, yet reciprocal ventilation potentially permits further substantial pressure attenuation. In a way, this concept functions like an internal 'iron lung'. Iron lungs were devices that externally encased the thorax, ventilating the patient by creating negative pressures instead of the positive pressures required for endotracheal mechanical ventilation. Iron lung ventilation is therefore closer to the physiological situation, causing less damage to the lungs than positive pressure ventilation. Reciprocal ventilation offers relief of lung strain by actively decreasing the insufflated carbon dioxide volume.

In some embodiments the invention is based on establishing an interaction between a ventilator device and an insufflator device such that changes in insufflator settings will have a substantially lesser negative influence on the effectiveness of the ventilator. The coupling between the two devices may e.g. allow an increase in ventilator mean airway pressure in anticipation of an increase in insufflator pressure, or vice versa. In addition, a complete stabilization of the body can be obtained by reciprocally changing the insufflated working space volume in conjunction with the volume that is ventilated in and out of the lungs.

In some embodiments the method pertains to adapting the insufflated volume to the pressure and/or volume changes caused by mechanical ventilation. This can be either in a responsive, triggered fashion, following the changes that are caused by ventilation, or by hardwired coupling to the ventilator to achieve synchronized pressure and/or volume adaptation. In some embodiments, the insufflator comprises elements to get the pressurized gas from the wall or cylinder to the trocar in the patient, at set pressure and with a max set flow. In addition, control features are provided to reduce the pressure when requested or when pressure is applied on the cavity, that are detected by sensor(s) (pressure and/or flow). The insufflation pressure can be synchronized with the ventilator by means of a hardwired connection to communicate with the ventilator. The control features comprise user input elements to set the pressure and flow, set a time offset in sync, set an offset in volume or pressure from the change made by the ventilator The invention can improve the ability to perform minimal access procedures by stabilizing surgical working space and decreasing the ventilation pressures that are required. The invention will also benefit the removal of excess $CO_2$ dissolved in body tissues due to the pressure of the insufflation and ventilation gases during thoracic and abdominal surgery, as the pressure of these gases can be better controlled and kept relatively low. It will enable the use of minimally invasive techniques in patient groups where the burden of conventional $CO_2$ insufflation is too great. Its concept can be utilized for both conventional positive pressure ventilation as well as for high-frequency oscillatory ventilation.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

The term "insufflator" is used to denote a device for exposing by insufflation of pressurized gas structures within a cavity of the human body for a diagnostic and/or therapeutic endoscopic procedure. Exemplary body cavities may be the thoracic or abdominal cavity. By insufflation, it is meant to insufflate an insufflation gas, most commonly $CO_2$ at controlled gas flow, gas output volume and/or gas output pressure in particular. The instantaneous pressure may be measured at sample rates of 0.1-500 Hz or even higher sample rates at least with a wave recognition up to 20 Hz in order to suitably predict and control the dynamics of the insufflated gas and dynamic response of the human body and body wall during gas insufflation. In the examples, insufflation may also encompass exsufflation, i.e. active removal of (part of) the insufflated volume.

The term 'insufflation rate' may denote a physical parameter, such as pressure, volume, temperature and frequency, that is adjusted in accordance with an instantaneous inflated lung volume, by means of hard-wired coupling with the ventilator or high-frequency internal or external pressure-and/or flow sensors.

The "breathing controller" may be a device singularly designed to match the insufflation rate to the breathing rate, directly or indirectly, for example, by measuring a breathing rate and having control logic to instruct the insufflator to change the insufflation rate. In more developed form, it matches the logic of a "ventilator", that is specifically designed for controlled ventilation of the lungs, in particular, control its inflated lung volume, e.g. by tracheal intubation, and delivering a controlled dose of ventilation gas, typically a composition of, amongst others, oxygen and nitrogen.

Both the insufflation gas and the ventilation gas may be conditioned, e.g. humidified by using a humidifier or brought to a certain temperature by a heating installation. The term 'real time' is indicated to substantially continuously measure and control, in contrast to isolated control that has a sample frequency larger than a breathing frequency. Typically, for real time measurement and control, a sample frequency of at least twice the breathing frequency is desirable.

The "insufflator controller" may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include microcontrollers, central processing units (CPUs), digital signal processors (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

Figure 1:
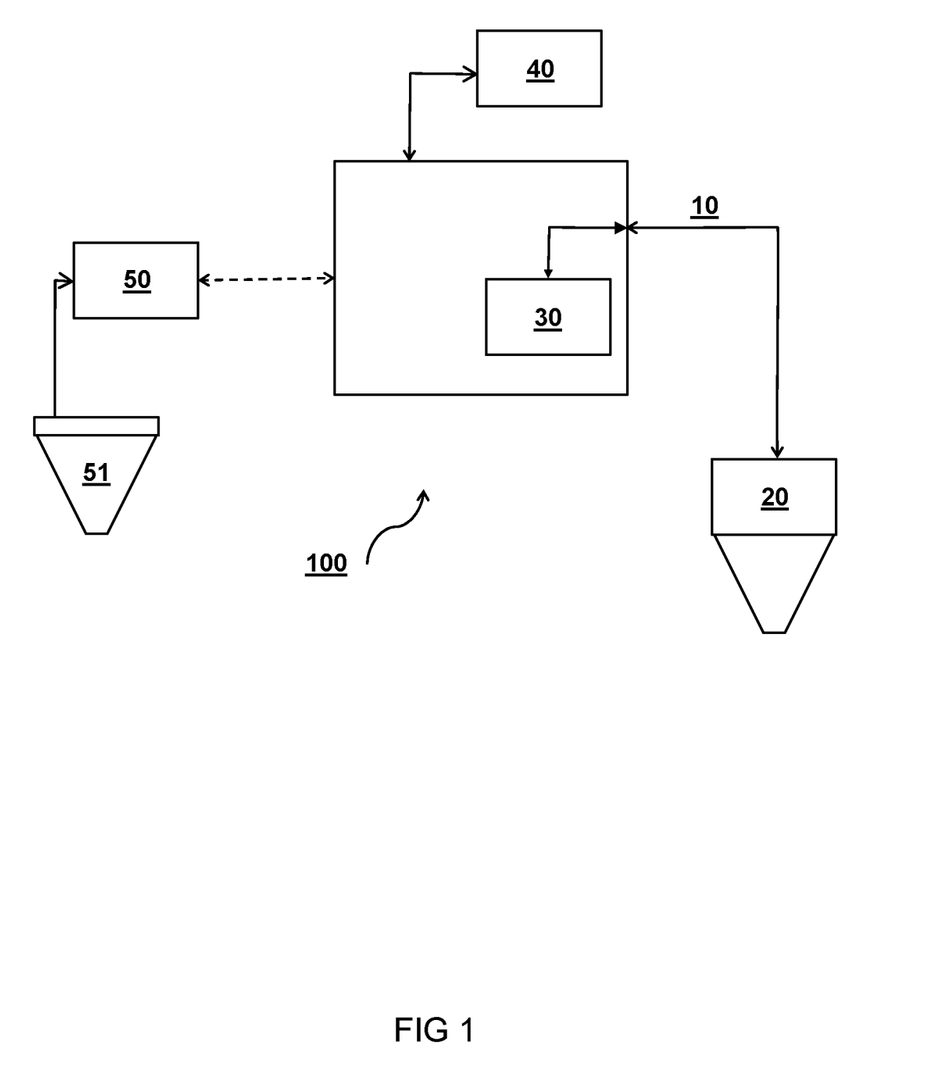
FIG. 1 schematically depicts a first embodiment according to an aspect of the invention.

In FIG. 1, an embodiment is disclosed, wherein the operation of the insufflator device 100 is shown in its simplest form. The system 100 intended for exposing an intended structure within a cavity of the human body for therapeutic and/or surgical treatment, comprises an insufflator 100. The insufflator comprising a gas output 10 and an insufflator input mechanism 20 adapted to input the gas from the gas output 10 into a cavity of a human body. A gas reservoir 30 may be present, wherein a suitable insufflation gas is stored, or the gas can be supplied via an external gas supply, e.g. a wall socket. This gas reservoir may by mechanically changing its volume provide in- and exsufflation. An insufflator controller 40 is provided for enlarging the cavity part by insufflation of gas from the gas output 10 into the cavity. A breathing controller 50 is provided.

The insufflator controller 40 is arranged to real time adapt an insufflation rate in accordance with an inflated lung volume and/or pressure detected from the breathing controller 50. Insufflator controller 40 and breathing controller 50 may be integrated in a single device and may share logic.

The inflated lung volume and/or pressure can be measured directly or indirectly, or may be derived from a model. In its simplest form, active forward control is possible by the insufflator, wherein breathing is mechanically imposed by the input mechanism 20. This is similar to an internal 'Iron Lung' ventilation, wherein the thoracic cavity is insufflated and actively desufflated at breathing frequency. In other forms a breathing controller 50 may also be a breathing detector, e.g. a mechanical sensor that detects the breathing, where the insufflator is adapted according to a breathing cycle. For instance, a sensor 51 can be provided for mechanical connection to the intended part of the human body to sense body wall motion. The motion signals are communicated to the insufflator controller to further adapt at least one of a gas flow, gas output volume and gas output pressure 10 of the insufflator 100, in order to suppress human body motion during ventilation of the lungs. The sensor 51 may also be connected to an intubation device 220 detecting the breathing cycle as shown in further forms elaborated herebelow with respect to FIGS. 7-8. The breathing controller 50 may be used for active mechanical ventilation, and the insufflator follows the mechanical ventilation cycle. The breathing controller 50 may receive input from an external breathing controller, e.g. from a ventilator, by an in/output connection, and/or from sensor 51. Exsufflated gas may be recirculated by storing it, e.g. in an internal column or in a compliant balloon. A piston switch may switch between in- and exsufflation mode; or this may be provided by a ventilator that switches between these modes.

Figure 2:
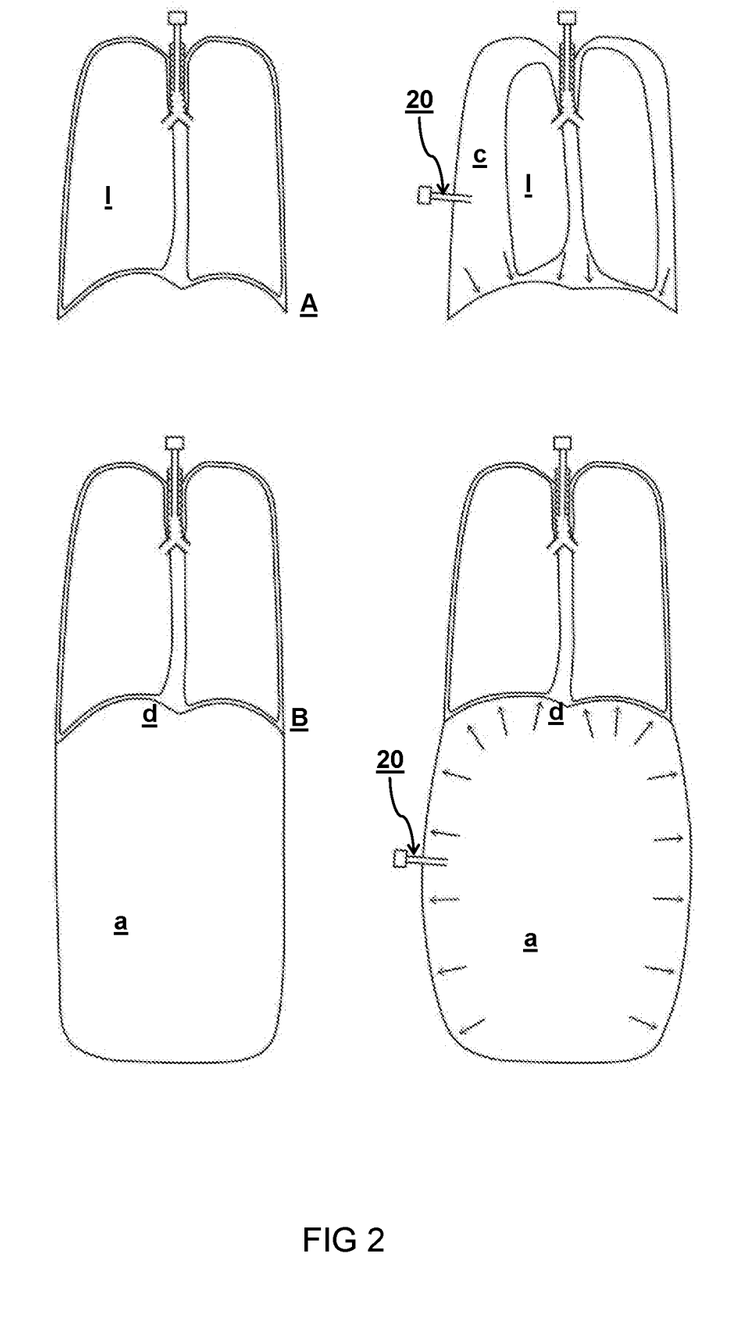
FIG. 2 schematically depicts the thoracic (A) and abdominal (B) cavity and the influence of insufflating a pressurized insufflation gas.

FIG. 2 shows in more detail the function of the input mechanism 20 when in conventional use. Typically, for minimally invasive surgery, the surgical instruments and an endoscopic camera are inserted into the thoracic (FIG. 2A) or abdominal cavity (FIG. 2B) or through trocars, that may simultaneously function as insufflator input mechanism 20. In some instance, the insufflator input mechanism 20 may be a trocar, that can be sealingly inserted in the cavity. In some embodiments, the trocar may have a venting mechanism that vents the insufflator output from the body cavity. Such an embodiment can be used when it is desired to (additionally) control the gas flow near the input mechanism of the insufflator. Such a venting mechanism may be passive, but the venting mechanism may also be actively operated by the insufflator controller. Additionally, the trocar can be used for insertion of a camera.

Figure 3:
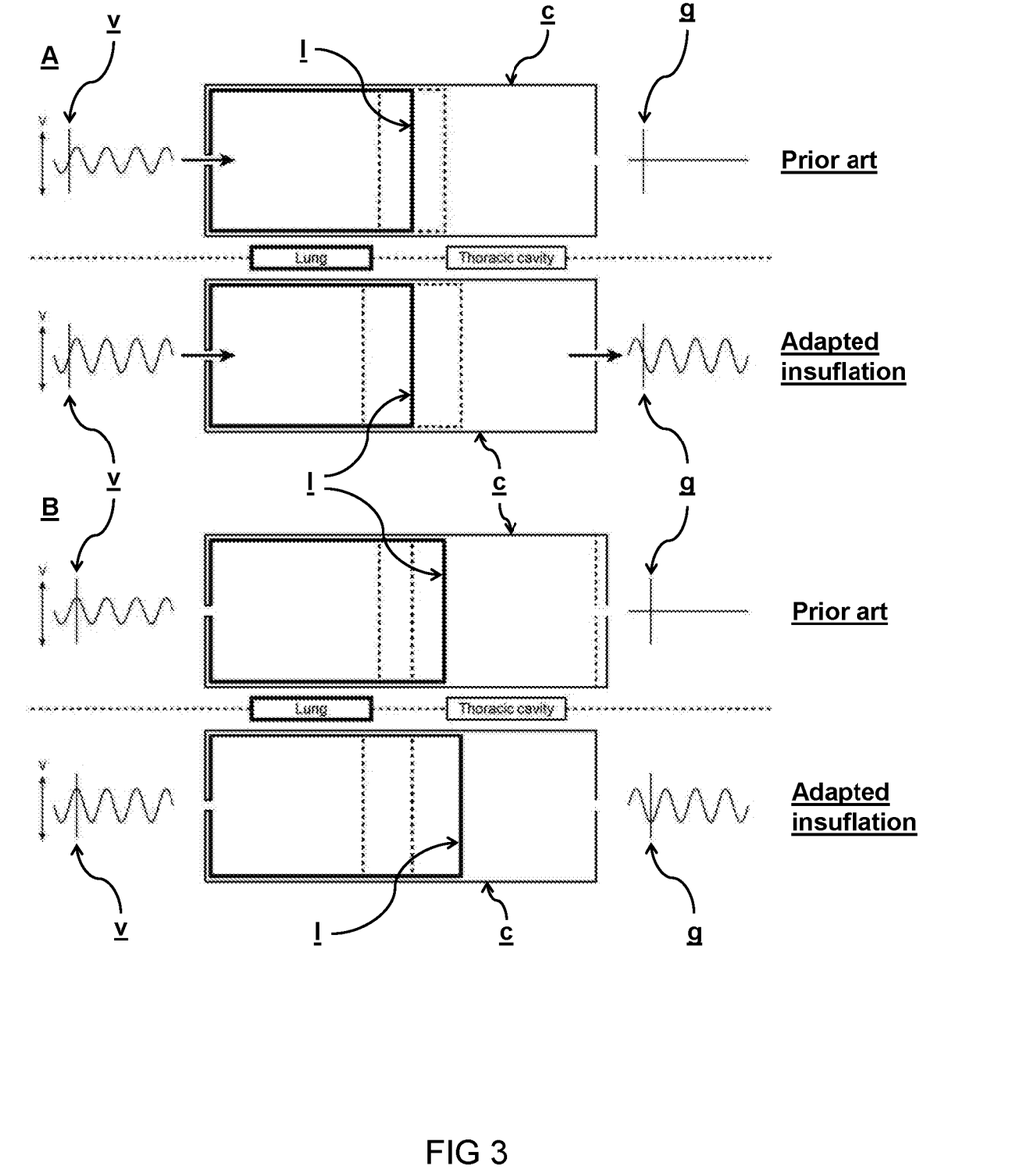
FIG. 3 shows exemplary respiratory phases during insufflation of the thoracic cavity, and the effect of conventional insufflation control respective to control according to an aspect of the invention.
Figure 4:
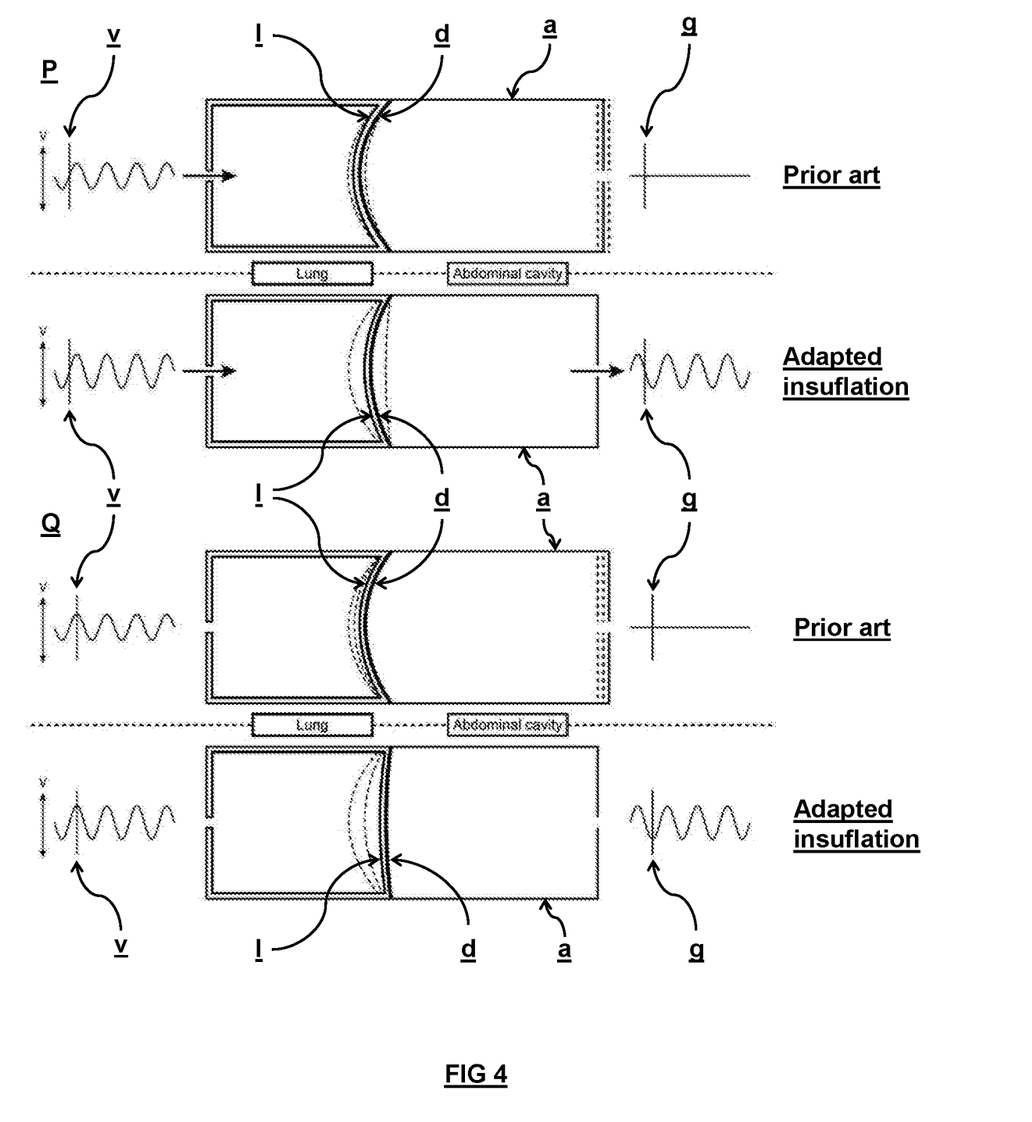
FIG. 4 shows exemplary respiratory phases during insufflation of the abdominal cavity, and the effect of conventional insufflation control respective to control according to an aspect of the invention.

Now turning to FIGS. 3 and 4, the working principle of the present invention is illustrated in subsequent phases ABCD of controlled ventilation of the lungs and abdomen in phases PQRS. As illustrated by the prior art version, current insufflators are devices that insufflate $CO_2$ gas g in the thoracic cavity c or abdominal cavity a to a set pressure, at a set flow rate g. This $CO_2$ gas pressure is conventionally maintained by measuring at a relatively low frequency of approximately 1 Hz or lower. This means that the current insufflators are by no means capable of following, and thereby adjusting to, the pressure changes that mechanical ventilation causes to the insufflated $CO_2$ volume. This is of particular interest when applied in the thoracic cavity c but may also apply for laparoscopic procedures in abdomen a, see FIG. 4. For the thoracic cavity the influence of mechanical ventilation is most prominent due to the limited elasticity of the thoracic wall in which the lungs 1 have to be inflated and deflated with each breath. In the abdominal cavity an insufflation pressure distends the abdomen and presses against diaphragm d, thereby limiting the ventilation of the lungs. Phases Q and S show improved inhalation and exhalation phases due to the insufflation cycle that is coordinated with the breathing cycle.

Conventionally the insufflated $CO_2$ volume, i.e. cavity c is maintained at a relatively static volume, due to the fact that the current equipment does not have the capability to adjust the volume per ventilated breath. As a consequence, higher ventilation pressures have to be applied, as illustrated in FIG. 3A to properly ventilate (and thereby distend) the lung 1 with each breath. Furthermore, the thoracic wall moves with each breath, due to the mechanical ventilation. In contrast, the insufflator controller according to an aspect of the invention, is arranged to real time adapt at least one of a gas flow, gas output volume and gas output pressure of the insufflator, in order to suppress or attenuate the movement of the body wall during mechanical ventilation of the lungs. Thus, in FIG. 3A, the thoracic cavity will be maintained relatively stable, where it is shown in FIG. 3B, that in this phase, while distending the lung, in the inhalation phase, also the thoracic cavity is expanded in the prior art situation. In contrast, by real time adaptation of the insufflation frequency rate in accordance with the breathing controller the thoracic cavity does not or only minimally expand, whereas the lungs can be mechanically ventilated with lower airway pressures.

In FIG. 3C, according to another aspect of the invention, it is illustrated that lung deflation is actively supported (see FIG. 3D) during the exhalation phase, which may result in also shortening this phase. It may also increase the working space volume during lung deflation by inputting $CO_2$ insufflation volume during this phase. In contrast, during inhalation, as shown in FIGS. 3A and 3B, $CO_2$ insufflation volume is actively or passively decreased up to a level at which the insufflation volume is to be maintained, resulting in a stabilization of the body wall with the trocars for the surgical instruments.

Thus, operating pressures of the active ventilation may be reduced as a result of real time adapting the insufflation frequency rate in accordance with the breathing rate. In addition, the working space may be temporary enlarged, for instance during intermittent positive pressure ventilation (IPPV), and in contrast to the prior art ventilation/insufflation, the body wall surrounding body cavity c can substantially stabilized.

In further embodiments illustrated in FIGS. 5, 6, 7 and 8. These figures describe four different manners of providing the required signal input for the breathing controller 50 of insufflator 100. The ventilation characteristics can be measured either by the insufflator 100, ventilator 200 or both. For this purpose they are equipped with sensors and the measurements are sent back to a breathing controller 50 and/or 60. The timing and characteristics could be shared by combining the I/O of the ventilator 2 and the I/O of the insufflator 1 that are wired together through 3. Data can be shared either from the insufflator to the ventilator, vice versa, or in both directions. To this end a control system is provided, as part of the insufflator, or as an external system, that may be used as incorporating the modified insufflator with a breathing controller. In particular the control system may comprise hardware and software components to implement a computer controlled method of operating an insufflator intended to expose an intended part in a cavity of the human body for therapeutic and/or surgical treatment, wherein a gas output from the insufflator and/or an gas input into the cavity of the human body are adapted by an insufflator controller to input gas from the gas output via the gas input into the cavity so as to enlarge the cavity part by insufflation of gas, wherein the insufflator controller real time adapts insufflation in accordance with a breathing rate of mechanical ventilation. The hardware parts may be provided with a computer program product comprising a non-transitory computer readable storage medium having instructions embodied thereon, which when executed by a computer cause the computer to execute the method herein disclosed. The ventilator is connected to tracheal intubation device 220, to mechanically ventilate the lungs 1. The insufflator is connected via input mechanism 20 to the thoracic cavity.

In some instance, the insufflator input mechanism may be a trocar, that can be sealingly inserted in the cavity. In some embodiments, the trocar may have a venting mechanism that vents the insufflator output from the body cavity. Such an embodiment can be used when it is desired to (additionally) control the gas flow near the input mechanism of the insufflator. Such a venting mechanism may be passive, but may be also be actively operated by the insufflator controller. Additionally, the trocar can be used for insertion of a camera.

Figure 5:
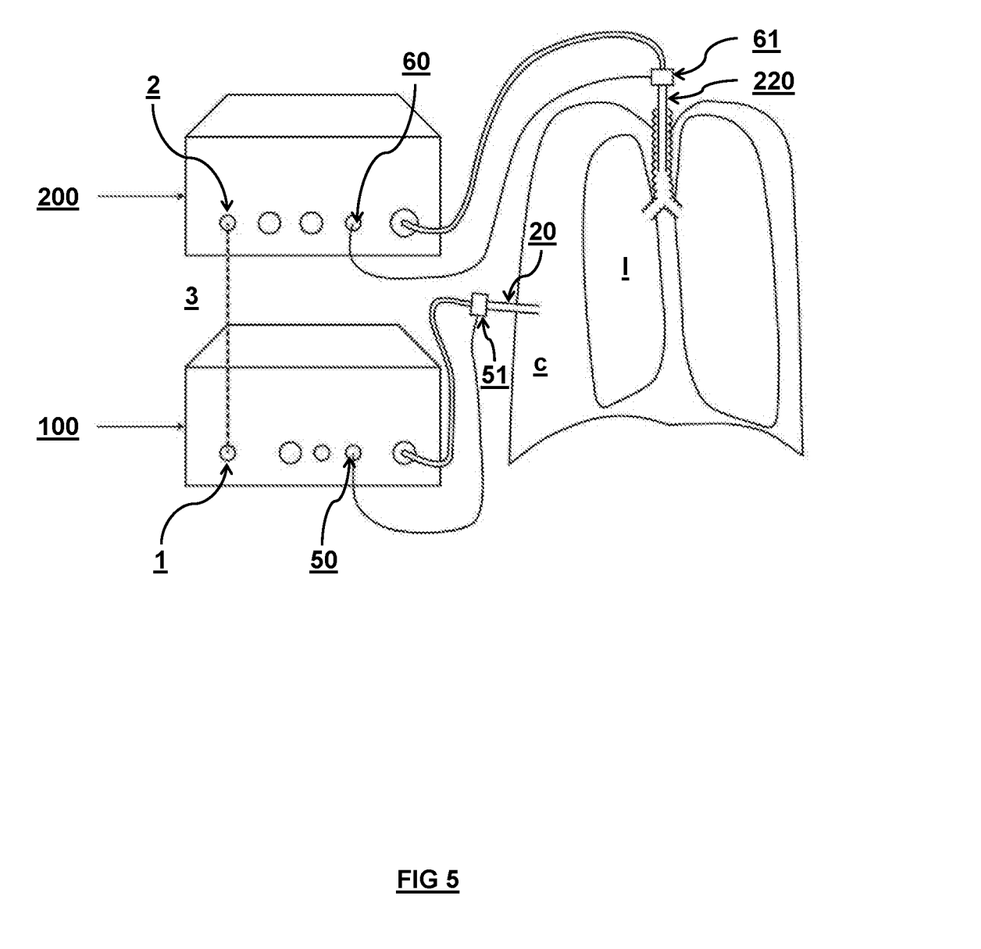
FIG. 5 schematically depicts a second embodiment according to an aspect of the invention.

In FIG. 5, via communication link 3 real time data are received and/or sent between I/O 1 and I/O 2, comprising at least one of a ventilation flow, ventilation output volume and ventilation output pressure values of the ventilator 200 and/or an insufflation flow, insufflation output volume and insufflation pressure values of the insufflator 100. The insufflator controller 40 is arranged to control the insufflator 100 in correspondence with the at least one of a ventilation flow, ventilation output volume and ventilation output pressure values received from the ventilator 200 via the breathing controller 50 as a breathing detector. A pressure and/or flow sensor 51 which is connected to the body cavity provides real time data comprising at least comprising of at least one of an insufflation flow, insufflation output volume and insufflation pressure values for feedback to the breathing controller 50 and/or insufflation controller 40.

Figure 6:
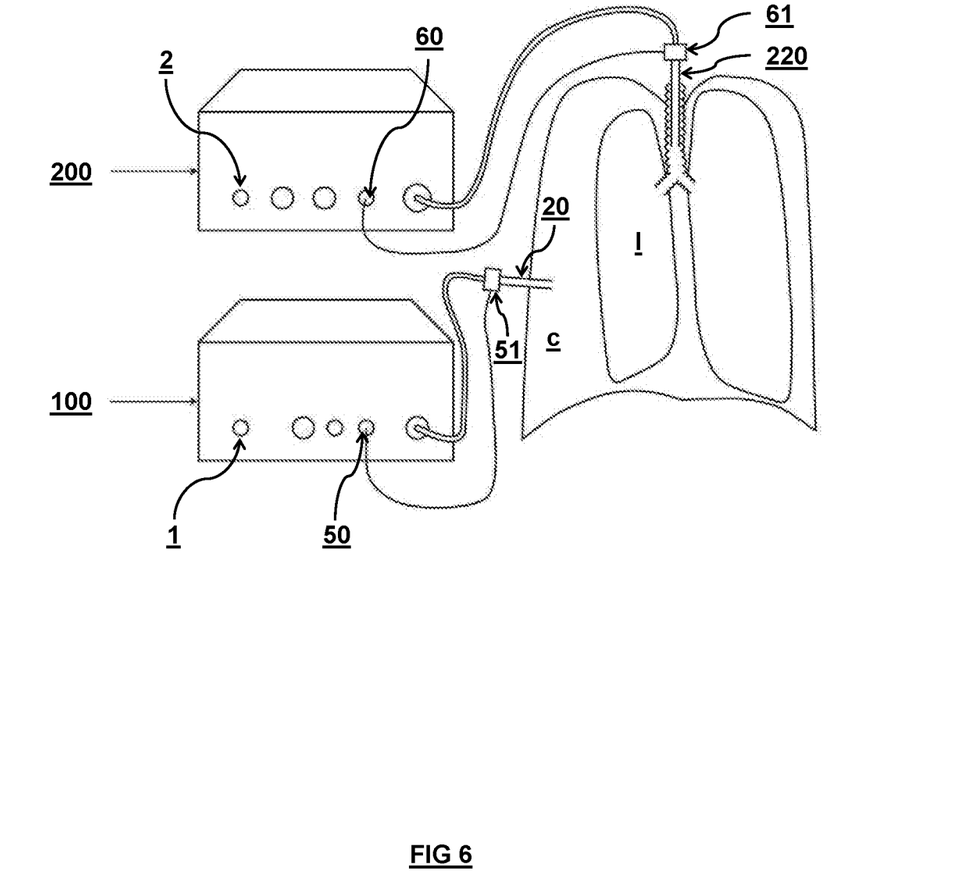
FIG. 6 schematically depicts a third embodiment according to an aspect of the invention.

In FIG. 6, a pressure and/or flow sensor 51 which is connected to the body cavity provides real time data comprising at least comprising of an insufflation flow, insufflation output volume and insufflation pressure values. The insufflator controller 40 is arranged to control the insufflator 100 in correspondence with at least one of an insufflation flow, insufflation output volume and insufflation pressure values, using these measurements from the insufflated body cavity as a breathing detector.

Figure 7:
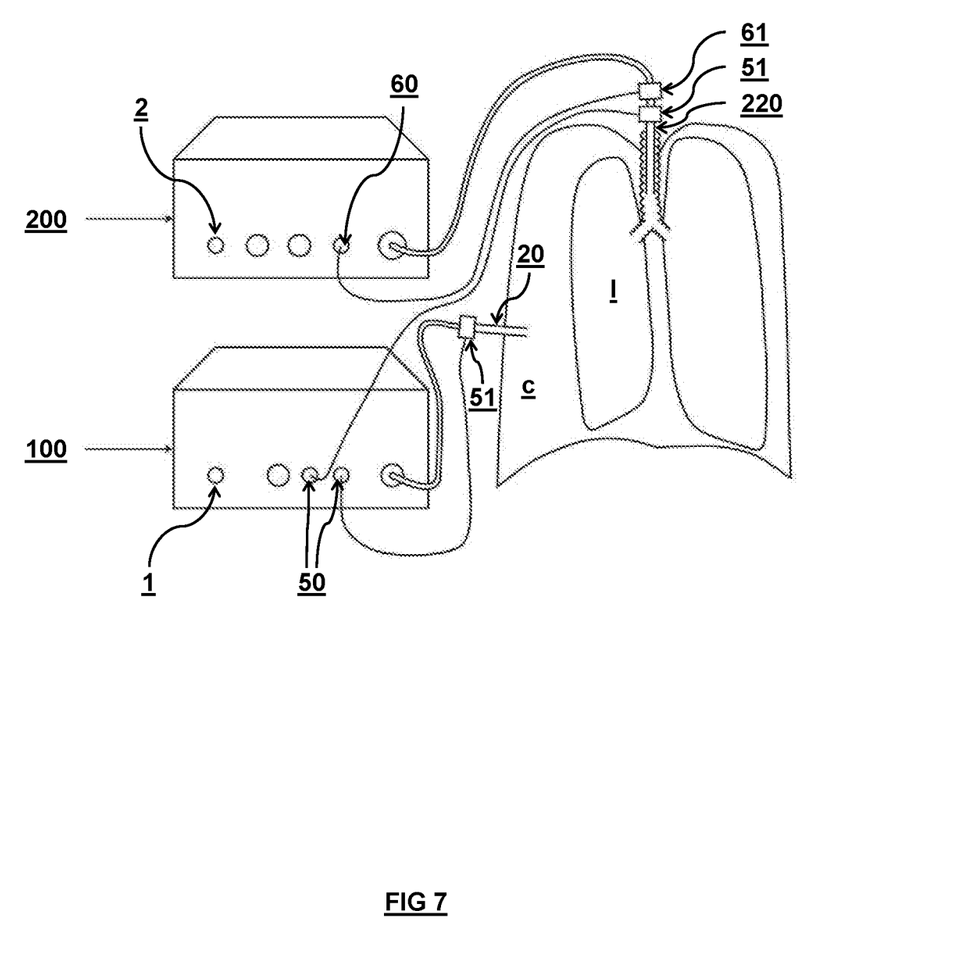
FIG. 7 schematically depicts a fourth embodiment according to an aspect of the invention.

In FIG. 7, pressure and/or flow sensors 51 are connected to both the body cavity, providing real time data comprising at least comprising of a ventilation flow, ventilation output volume and ventilation pressure values, as well as to an intubation device 220, providing real time data comprising at least comprising of an insufflation flow, insufflation output volume and insufflation pressure values. The insufflator controller 40 is arranged to control the insufflator 100 in correspondence with at least one of an insufflation flow, insufflation output volume and insufflation pressure values provided through breathing controller 50, using these measurements from the sensor 51 at the intubation device 220 as a breathing detector.

Figure 8:
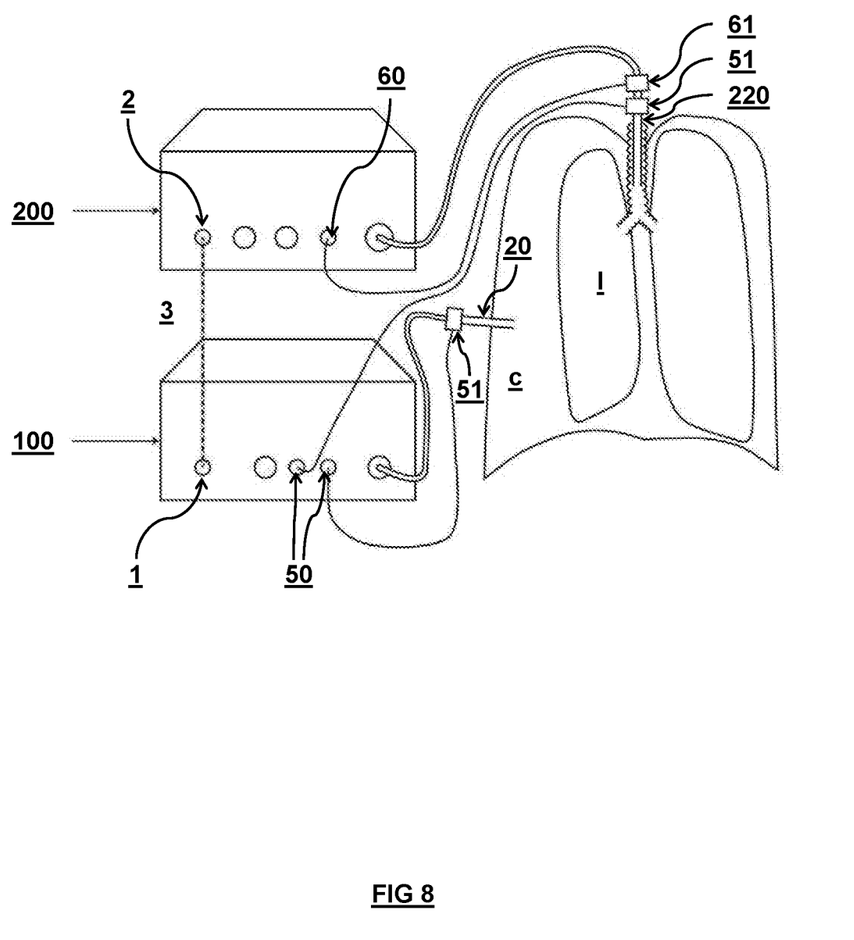
FIG. 8 schematically depicts a fifth embodiment according to an aspect of the invention.

In FIG. 8, pressure and/or flow sensors 51 are connected to both the body cavity, providing real time data at least comprising of a ventilation flow, ventilation output volume and ventilation pressure values, as well as to an intubation device 220, providing real time data at least comprising of an insufflation flow, insufflation output volume and insufflation pressure values. The insufflator controller 40 is arranged to control the insufflator 100 in correspondence with at least one of an insufflation flow, insufflation output volume and insufflation pressure values provided through breathing controller 50, using these measurements from the sensor 51 at the intubation device 220 as a breathing detector. Via communication link 3 real time data comprising at least one of a ventilation flow, ventilation output volume and ventilation output pressure values as measured at the intubation device 220 by the there placed sensor 51 are transmitted from insufflator 100 to ventilator 200.

Further Embodiments

While the preceding examples show a conventional mechanical ventilation embodiment, the inventors also envisage application of aspects of this invention in combination with high-frequency oscillatory ventilation (HFOV) The following advantages may be achieved:

a) Aspects of the invention as described herein may result in substantial attenuation of airway pressure caused by a relatively static insufflation volume. The pressure wave of mechanical ventilation is currently attenuated in both directions by the static volume of insufflated $CO_2$.

b) This invention may solve/reduce movement of the body wall caused by mechanical ventilation and patient shaking caused by HFOV. The pressure changes that are applied to the lung in mechanical ventilation are propagated by the static insufflated $CO_2$ gas volume to the entire body wall. Applying a insufflator-generated counter wave neutralizes this effect, limiting all movement to just the lungs. This eliminates unwanted and deleterious movement of the trocars and therewith the surgical instruments during delicate surgical procedures.

c) High-frequency oscillatory ventilation is per ventilation device limited to a certain patient size by its mechanical power. Dampening of the effectiveness of the oscillations by the static $CO_2$ insufflation volume limits the patient size at which a specific ventilator can be used. Removing pressure attenuation permits the effective application of a less powerful HFO ventilator for larger patients.

While it is desired to make minimal access surgery possible in even the smallest of children, however, the conventional procedures often cannot be performed using minimally invasive techniques due to the limited surgical working space and suboptimal ventilation conditions. The present invention improves the ability to perform minimal access procedures on children by stabilizing surgical working space and decreasing the ventilation pressures that are required. However, not only (young) children but also other patients groups may benefit substantially from this invention. The morbidly obese e.g. require very high insufflation and ventilation pressures resulting from their very high body mass, which may be reduced by the invention.

One improvement that is part of a particularly preferred embodiment in aspects of this invention concerns coupling of the insufflator to the ventilator to couple gas insufflation to the ventilation and preferably to the inflated lung volume. This facilitates the precise timing and adjustments required for application during surgery under mechanical ventilation.

The invention may provide constant pressure insufflation, or alternatively, volume and/or pressure controlled insufflation.

In high-frequency oscillatory ventilation insufflation can be synchronized with ventilation, e.g. in a reciprocal fashion, to match ventilated tidal volumes. In- and exsufflated volumes can be greater than ventilated tidal volumes and/or smaller than ventilated tidal volumes.

In alternative embodiments, insufflation may be phase-shifted with identical frequency. During intermittent positive pressure ventilation (IPPV) insufflation can be synchronized, to result in equal volumes, and/or volumes greater than ventilated tidal volumes and/or volumes smaller than ventilated tidal volumes. Also, insufflation may be asynchronously phase-shifted insufflation with identical frequency. In an alternative embodiment, in IPPV insufflation volume adaptation can be triggered.

Alternatively switching may be provided between IPPV and high-frequency oscillatory ventilation.

In further embodiments, the coupling of ventilator and insufflator systems as presently disclosed are tested ex-vivo in a model in which the body wall and lungs are mechanically modeled. Varying size and compliance permits optimization before progressing to in-vivo studies.

After ex-vivo testing, a prototype of the device is tested and optimized in an animal model of thoracic and abdominal minimal access surgery. This allows extensive monitoring of vital signs and determination of surgical working space with intra-procedural computed tomography.

Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims.

Advantage

The present invention may have following advantages. By establishing a connection between an insufflator and a ventilator for conventional positive pressure ventilation the coupled insufflator may actively support lung deflation shortening the exhalation phase. It may also improve ventilation during lung deflation by adding $CO_2$ insufflation volume during this phase. During inhalation the $CO_2$ insufflation volume is actively decreased until a level at which the insufflation volume is to be maintained.

The advantages are substantial in case of the use of high-frequency oscillatory ventilation (HFOV), which is a particularly viable technique for minimal access surgery in neonates. Every year, thousands of children need surgery. Even though many of these procedures are considered relatively simple, only one-third of these procedures to be performed using minimally invasive techniques. Only one-fifth of the complex procedures can be performed using minimally invasive techniques. According to an aspect, this invention may increase the percentage of procedures that can be performed using minimally invasive techniques.

The advantages when applying this invention can be multiple:

1. It can solve attenuation of airway pressure caused by a relatively static insufflation volume and may prevent lung injury from over distension. The pressure wave of mechanical ventilation is currently attenuated in both directions by the static volume of insufflated $CO_2$.

2. It can reduce or even completely eliminate movement of the body wall caused by mechanical ventilation and patient shaking caused by HFOV. The pressure changes that are applied to the lung in mechanical ventilation are propagated by the static insufflated $CO_2$ gas volume to the entire body wall. Applying a insufflator-generated counter wave neutralizes this effect, limiting all movement to just the lungs. This eliminates unwanted and deleterious movement of the trocars and therewith the surgical instruments during delicate surgical procedures.

3. A high-frequency oscillatory ventilation device is conventionally limited to a certain patient size by its mechanical power. Dampening of the effectiveness of the oscillations by the static $CO_2$ insufflation volume limits the patient size at which a specific ventilator can be used. Removing pressure attenuation permits the effective application of a less powerful HFO ventilator also for larger patients.

Another example of significant benefit from this invention is in patients in which ventilation and/or insufflation pressures are particularly high, e.g. in obesity surgery. The high insufflation pressures that are required during laparoscopic intra-abdominal procedures push the diaphragm upward, severely limiting the movement of the artificially ventilated lungs. As a consequence, higher ventilation pressures are required to counter this effect of high insufflation pressures. Reciprocal insufflation allows attenuation of the required ventilation pressures by exsufflation of gas from the abdomen during the inhalation phase of the ventilator. This allows the lungs and diaphragm to move down while maintaining a stable surgical working space and intra-abdominal insufflation pressure.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. As described above, the exemplary embodiments can be in the form of computer-implemented processes and apparatuses for practicing those processes. The exemplary embodiments can also be in the form of computer program code containing instructions embodied in tangible media, such as floppy diskettes, CD ROMs, hard drives, or any other computer-readable storage medium, wherein, when the computer program code is loaded into and executed by a computer, the computer becomes an apparatus for practicing the exemplary embodiments. The exemplary embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes an apparatus for practicing the exemplary embodiments. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. An apparatus for exposing structures within a cavity of the human body for diagnostic and/or therapeutic endoscopic procedure, comprising:
   an insufflator, comprising a gas output and an insufflator input mechanism adapted to input gas from the gas output into the cavity of the human body, the insufflator further comprising an insufflator controller for enlarging the cavity part by insufflation of said gas from the gas output into the cavity; and
   a breathing controller arranged to detect one or more types of a status information taken from the group consisting of:
   an inflated lung pressure per breath, and an inflated lung volume per breath;
   wherein the insufflator controller is arranged to real time adapt an insufflation rate of said gas, to adjust, per breath detected by the breathing controller, the insufflated volume output into the cavity, in accordance with one or more types of the status information.

2. An apparatus according to claim 1, wherein the insufflator controller is arranged to real time adapt an insufflation phase in accordance with a detected breathing phase of the human body.

3. The apparatus according to claim 2, wherein the insufflator controller is arranged to adapt the insufflation phase from the detected breathing phase of a mechanical ventilator.

4. The apparatus according to claim 2, wherein the insufflator controller is arranged to keep an insufflation frequency and a breathing rate in shifted phases.

5. The apparatus according to claim 1, wherein, in order to suppress human body wall motion during mechanical ventilation of the lungs, the insufflator controller is arranged to real time adapt at least one of the group consisting of: a gas flow, gas output volume and gas output pressure of the insufflator.

6. The apparatus according to claim 1, wherein the insufflator controller is adapted to be communicatively coupled with a ventilator controller of a ventilator for controlled ventilation of the lungs, to real time receive at least one of the group of parameters consisting of; ventilation flow, ventilation output volume or ventilation output pressure of the ventilator, and wherein the insufflator controller is arranged to control the insufflator in correspondence with at least one of said parameters received from the ventilator controller.

7. The apparatus according to claim 6, wherein the ventilator controller comprises at least one of the group consisting of: a ventilation flow meter and ventilation pressure detector to measure at least one of a ventilation flow, ventilation output volume and ventilation output pressure of the ventilator, and to real time transmit at least one of the group of ventilation parameters consisting of: a ventilation flow, ventilation output volume and ventilation output pressure of the ventilator to the insufflator controller.

8. The apparatus according to claim 6, wherein the ventilator controller is adapted to real time receive from the insufflator controller at least one of the group of gas parameter values consisting of: a gas flow, gas output volume and gas output pressure of the insufflator, to real time adapt at least one of the group of ventilator parameter values consisting of: a ventilation flow, a ventilation volume, ventilation gas and ventilation pressure output of the ventilator.

9. The apparatus according to claim 1, wherein the insufflator comprises a detector:
   communicatively coupled to the insufflator controller,
   arranged to measure at least one of the group consisting of: a gas flow, gas output volume and gas output pressure at the insufflator gas output.

10. The apparatus according to claim 1, wherein the insufflator comprises a further detector arranged to measure at least one of a gas flow, gas output volume and gas output pressure and gas temperature at a distal part of the insufflator input mechanism.

11. The apparatus according to claim 1, further comprising a motion sensor for mechanical connection to the body wall of a cavity of the human body to sense a body wall motion, wherein the motion signals are communicated to the insufflator controller to further adapt at least one of a gas flow, gas output volume and gas output pressure of the insufflator, in order to suppress human body motion during mechanical ventilation of the lungs.

12. The apparatus according claim 1, wherein the insufflator input mechanism is a trocar, that can be sealingly inserted in the cavity.

13. A computer controlled method of operating an insufflator intended to expose an intended structure within a cavity of the human body for a diagnostic and/or therapeutic endoscopic procedure, the method comprising:
  adapting, by an insufflator controller, a gas output from the insufflator and/or an gas input into the cavity of the human body to input gas from the gas output via the gas input into the cavity so as to enlarge the cavity part by insufflation of gas,
  wherein, during the adapting, the insufflator controller adapts, per breath detected by a breathing controller, in real time an insufflation frequency and flow rate in accordance with one or more types of a status information taken from the group consisting of:
  an inflated lung pressure per breath, and
  an inflated lung volume per breath.

14. A computer program product comprising a non-transitory computer readable storage medium having instructions embodied thereon, which when executed by a computer, cause the computer to execute a method of operating an insufflator intended to expose an intended structure within a cavity of the human body for a diagnostic and/or therapeutic endoscopic procedure, where the method comprises:
  adapting, by an insufflator controller, a gas output from the insufflator and/or a gas input into the cavity of the human body to input gas from the gas output via the gas input into the cavity so as to enlarge the cavity part by insufflation of gas,
  wherein, during the adapting, the insufflator controller adapts, per breath detected by a breathing controller, in real time an insufflation frequency and flow rate in accordance with one or more types of a status information taken from the group consisting of:
  an inflated lung pressure per breath, and
  an inflated lung volume per breath.

* * * * *